United States Patent
Kawamura et al.

Patent Number: 6,046,805
Date of Patent: Apr. 4, 2000

[54] METHOD AND APPARATUS FOR TRANSFUSING LIQUID SPECIMEN FOR OPTICAL CHARACTERISTIC MEASUREMENT AND POLARIMETER USING THE SAME

[75] Inventors: Tatsurou Kawamura, Kyotanabe; Jinsei Miyazaki, Higashiosaka, both of Japan

[73] Assignee: Matsushita Electric Industrial Co., Ltd., Osaka-fu, Japan

[21] Appl. No.: 09/159,502

[22] Filed: Sep. 23, 1998

[30] Foreign Application Priority Data

Sep. 24, 1997 [JP] Japan ................................. 9-258787

[51] Int. Cl.$^7$ .............................. G01N 21/01; G01J 4/00
[52] U.S. Cl. ..................... 356/244; 356/246; 356/432; 356/440; 356/441; 356/442; 356/364; 356/367; 356/368
[58] Field of Search ..................... 356/364, 367, 356/368, 244, 246, 432, 440, 441, 442

[56] References Cited

U.S. PATENT DOCUMENTS

| | | |
|---|---|---|
| 3,699,348 | 10/1972 | Höcherl . |
| 3,740,151 | 6/1973 | Chaney et al. ........................ 356/117 |
| 4,589,776 | 5/1986 | Carver et al. ......................... 356/367 |
| 4,900,512 | 2/1990 | Meyrat et al. . |
| 4,902,134 | 2/1990 | Spanier ................................. 356/364 |
| 4,988,199 | 1/1991 | Paul ..................................... 356/368 |
| 5,182,617 | 1/1993 | Yoneyama et al. . |

FOREIGN PATENT DOCUMENTS

| | | |
|---|---|---|
| 2 674 959 | 10/1992 | France . |
| WO97/18470 | 5/1997 | WIPO . |

*Primary Examiner*—Frank G. Font
*Assistant Examiner*—Roy M. Punnoose
*Attorney, Agent, or Firm*—McDermott, Will & Emery

[57] ABSTRACT

An apparatus and a method for transfusing liquid specimen for an optical characteristic measurement, which is excellent in operability and handling, and capable of introducing a liquid specimen into a sample cell without detaching the cell from an optical characteristic measurement apparatus and without bubbling, as well as a polarimeter are disclosed. According to the present invention, the specimen can be introduced into the sample cell without detaching the sample cell from the equipment, in a way of connecting the bottom of the sample cell with a reservoir for temporarily accommodating the liquid specimen through a tubular path, then varying a difference in the levels of the sample cell and the reservoir, or a way of using a syringe arranged in the tubular path. At expelling the specimen from the sample cell, the specimen is transfused into the reservoir in a similar manner.

21 Claims, 6 Drawing Sheets

METHOD AND APPARATUS FOR TRANSFUSING LIQUID SPECIMEN FOR OPTICAL CHARACTERISTIC MEASUREMENT AND POLARIMETER USING THE SAME

BACKGROUND OF THE INVENTION

The present invention relates to an apparatus for measuring an optical characteristic of a liquid specimen in order to determine a purity thereof, to identify and to determine a concentration of a solute contained therein, and particularly relates to a polarimeter applicable to an urinalysis apparatus. More specifically, the present invention relates to an apparatus and a method for transfusing a liquid specimen into a sample cell for the measurement.

In general, optical characteristics, for instance, absorbance and optical activity, of a specimen are derived by projecting a light onto the specimen accommodated in a sample cell and analyzing a light transmitted through the specimens. As the sample cell, a box-shaped container mainly made of glass having a pair of transparent light-transmitting windows is used.

The measurement on such optical characteristics has conventionally been conducted by introducing the specimen into the sample cell through the open top end thereof by using a squirt, a pipette, a syringe or the like, and installing the sample cell in an optical system. In this procedure, for introduction or exhaustion of the specimen, and for washing the sample cell, there is required a detachment of the sample cell from the optical system. As shown, the measurement on the optical characteristics was poor in operability and required much man power. In addition, if bubbles exist in an optical path of the sample cell, the obtained measurement values are liable to show uneven values.

Recently, an urinalysis using a polarimeter is proposed, for instance, in International Patent Publication No. WO97/18470. Glucose or a protein i.e., albumin demonstrates an optical activity. It is therefore possible to derive concentrations of these substance in a urine by conducting a polarimetry on the urine. In the conventional urinalysis, a test paper impregnated with a reagent was dipped into the urine and the color reaction thereof was observed by spectrophotometer or the like. On the contrary, it is possible to detect and to determine glucose and protein in a low concentration without requiring any expendable supplies such as test papers as required in the conventional urinalysis, according to this method.

BRIEF SUMMARY OF THE INVENTION

An object of the present invention is to solve the above-mentioned problems inherent to the conventional optical characteristic measurement apparatus. The present invention provides an apparatus for transfusing a liquid specimen, which permits easy introduction and exhaustion of the specimen as well as easy washing of the sample cell, and enables a measurement with high accuracy free from inclusion of bubbles in the specimen to be measured and their disturbance on the optical path.

Another object of the present invention is to provide a polarimeter and an urinalysis equipment which are compact and high in reliability at a low price.

A method for transfusing a liquid specimen for an optical characteristic measurement of the present invention employs an optical characteristic measurement apparatus comprising: a reservoir for temporarily accommodating a liquid specimen to be measured; a sample cell for holding the specimen and for permitting a projected light to transmit through the held specimen; and a tubular path for connecting between the sample cell at the portion being in contact with the held specimen and the reservoir.

The method includes the steps of;

supplying a specimen into the reservoir;

allowing the reservoir to stand for a certain time; and introducing the specimen accommodated in the reservoir into the sample cell through the tubular path.

The present invention enables the introduction and replacement of the liquid specimen without detaching the sample cell from the optical characteristic measurement apparatus. In the present invention, the specimen contemporarily accommodated in the reservoir is introduced into the sample cell via a tubular path which connects the bottom of the sample cell and the reservoir, by utilizing a difference in the vertical levels between the sample cell and the reservoir. Alternatively, the specimen in the reservoir is introduced into the sample cell by using a syringe interposed on the tubular path. At expelling the specimen after finishing the measurement, it is likewise transfused from the sample cell to the reservoir.

The specimen introduced into the sample cell is transfused into the reservoir, and then expelled therefrom.

At washing the sample cell, a cleaning solution is supplied to the reservoir after expelling the specimen which had been transfused from the sample cell. Then, the cleaning solution is introduced into the sample cell through the tubular path. The cleaning solution introduced into the sample cell is then transfused into the reservoir and expelled therefrom.

In a state where the specimen introduced thereinto remains in the sample cell, it is possible to supply another liquid specimen to be measured or a cleaning solution to the sample cell, thereby to expel the specimen remaining in the sample cell, and simultaneously, to relpace the remaining specimen with the other liquid specimen or the cleaning solution.

By moving the reservoir or the sample cell upwards and downwards for giving a difference in the height between the both, it is possible to transfuse the specimen or the cleaning solution between the reservoir and the sample cell.

In that process, by arranging the syringe so as to direct the plunger upward, it is possible to trap the bubbles in the sucked-up specimen in the syringe and collect them at upper portion of the plunger, and thus to introduce the specimen free from the bubbles into the sample cell.

Another method for transfusing a liquid specimen for an optical characteristic measurement of the present invention employs an optical characteristic measurement apparatus comprising: a reservoir for temporarily accommodating a liquid specimen to be measured; a sample cell for holding the specimen and for permitting a projected light to transmit through the specimen; and a tubular path for connecting between the reservoir at a portion immersed in the specimen and the sample cell. The method comprises the steps of:

injecting a specimen or a cleaning solution into the reservoir; and introducing the specimen or the cleaning solution accommodated in the reservoir into the sample cell through the tubular path by sucking it up through an opening arranged at the top end of the sample cell.

The specimen held in the sample cell is expelled by sucking it up from the opening.

In a state where the specimen or the cleaning solution introduced remains in the sample cell, it is possible to further introduce another liquid specimen or cleaning solution into the sample cell thereby, to expel the previously introduced specimen or cleaning solution remaining in the sample cell, and simultaneously, to replace it.

An apparatus for transfusing a liquid specimen for an optical characteristic measurement of the present invention comprises:

- a reservoir for temporarily accommodating a liquid specimen to be measured;
- a sample cell for holding the specimen and for permitting a projected light to transmit through the specimen;
- a tubular path for connecting the bottom of the sample cell with the reservoir at a portion where it is immersed in the specimen; and
- an elevator for moving at least one of the reservoir and the sample cell upward and downwards.

Another apparatus for transfusing a liquid specimen for an optical characteristic measurement of the present invention comprises; a three-way cock whose one channel is connected to a sample cell for holding a liquid specimen to be measured, and a syringe and a reservoir for accommodating the specimen, each connected to one of the other two channels of the three-way cock, respectively.

Still further apparatus for transfusing a liquid specimen for an optical characteristic measurement of the present invention comprises: a syringe which is connected to a sample cell for holding a liquid specimen for expelling the specimen from the cell. By connecting the syringe with the sample cell through the three-way cock, it is possible to expel the specimen from the sample cell through an open channel of the three-way cock.

The above-mentioned apparatuses for transfusing liquid can be applied to, for instance, a polarimeter which measures concentrations of fructose, sucrose, glucose, and the like in an aqueous solution.

In particular, by applying it to a polarimeter comprising:

- a monochrome light source for projecting a substantial parallel light;
- a polarizer for transmitting only a polarized component in a specified direction of the substantial parallel light;
- a sample cell for holding a liquid specimen to be measured so arranged that the substantial parallel light transmitted through the polarizer can transmit therethrough;
- a coil for applying a magnetic field in the direction of an optical path of the substantial parallel light transmitting through the specimen in the sample cell;
- a current source for flowing a current through the coil;
- a magnetic filed sweeping means for sweeping the current to be flown through the coil;
- a magnetic field modulating means for modulating the current to be flown through the coil;
- an analyzer for transmitting only a polarized component in another specified direction of the light transmitted through the specimen;
- a photosensor for detecting the light transmitted through the analyzer;
- a lock-in amplifier for conducting a phase sensitive detection on an output signal of the photosensor with reference to a vibration modulating signal outputted from the magnetic field modulating means; and
- a processing unit for calculating an optical activity of the specimen based on the magnetic field sweeping signal of the magnetic field sweeping means and the output signal from the lock-in amplifier. The above-mentioned application realizes a polarimeter which can easily perform a polarimetry (measurement of angle of rotation).

By performing the polarimetry on the urine using this polarimeter in particular, it is possible to derive glucose and albumin concentrations in the urine with ease and high accuracy. Therefore, it is possible to provide an excellent urinalysis equipment.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

The apparatus for transfusing liquid in accordance with the present invention can be applicable to diversified optical characteristics measurement apparatuses for various liquid specimens.

In the following embodiments, a description will be made on, as an example of the optical characteristic measurement apparatus, a polarimeter, in particular, a polarimeter of magnetic field application-type (optical Faraday modulator-type), which give a concentration of an optically active substance in the specimen by applying a magnetic field on the light transmitting through the specimen and compensating the angle of rotation attributable to the optically active substance in the specimen with that attributable to the application of the magnetic field.

EXAMPLE 1

Figure 1:
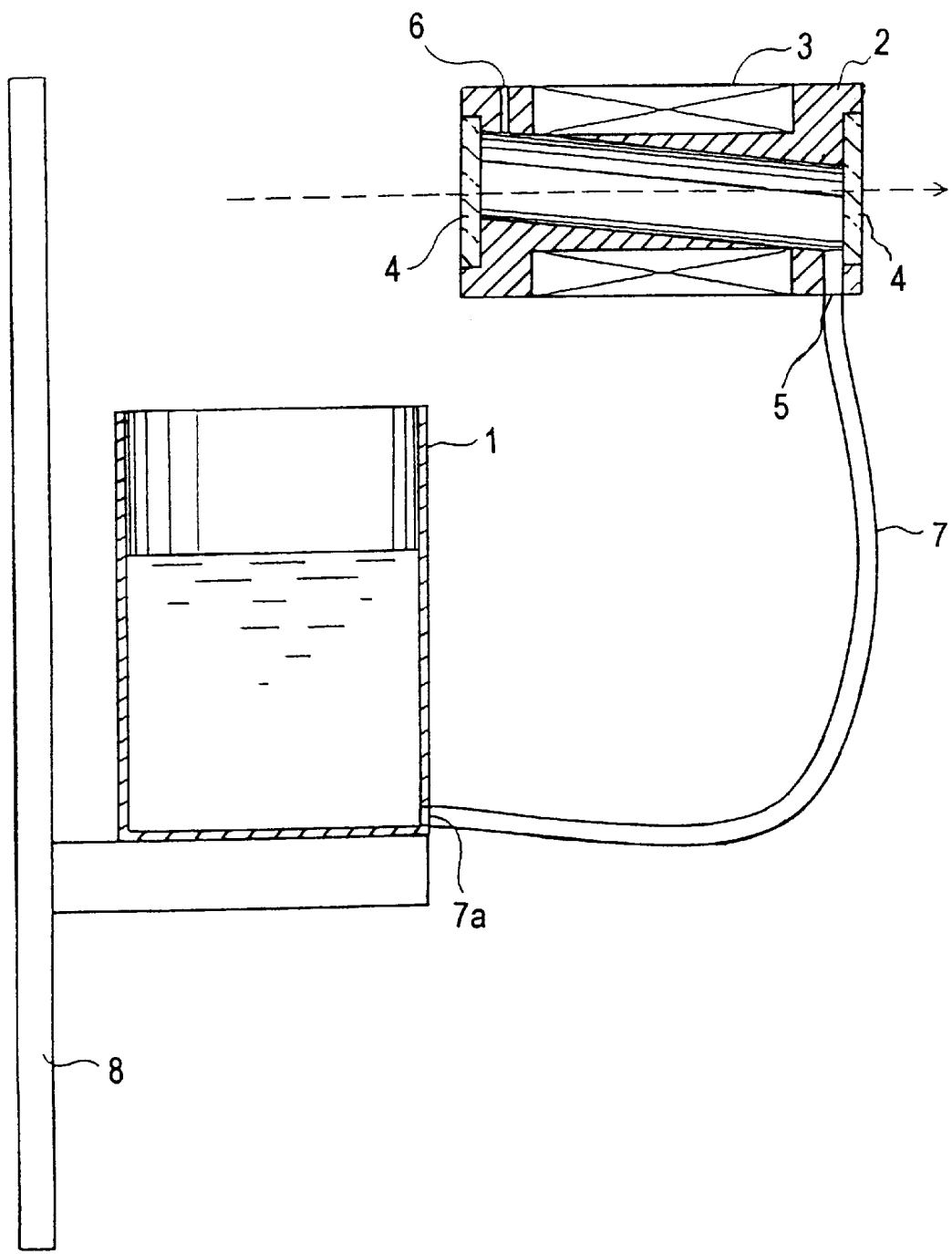
FIG. 1 is a schematic view for showing the configuration of an apparatus for transfusing liquid in one embodiment of the present invention.

The apparatus for transfusing liquid in this embodiment will be described with reference to FIG. 1.

A reservoir 1 temporarily accommodates a sampled liquid specimen. A sample cell 2 holds the specimen supplied from the reservoir 1. By permitting a light to transmit therethrough in the direction indicated by an arrow in the figure, an optical characteristic of the specimen held in the sample cell 2 is measured. The sample cell 2 has an optical path of 50 mm and can hold the specimen of about 5.7 cc.

The sample cell 2 is obtained by working in the following manner.

First, by cutting side faces of a rectangular aluminum block along the longer axis (length of 55 mm), a cylindrical part with a diameter of 17 mm is formed on the center thereof, while leaving untouched parts each having a width of 10 mm on the both ends. Then, a cylindrical cavity having a diameter of 12 mm and an axis inclined by about 5.7 degrees ($\tan^{-1}$ (5/50)) with respect to the longer axis is provided between the both end faces. On the both end faces of the cavity, holes with a diameter of 22 mm and a depth of 2.5 mm are provided, and glass disks 4 with a diameter of 22 mm and a thickness of 2.5 mm are tightly fitted into the holes, respectively.

Surrounding the outer circumference of the cut cylindrical part of the sample cell 2, a coil 3 is provided for applying a magnetic field to the specimen held in the sample cell 2. The coil 3 is configured by winding an enameled wire with a diameter of 0.7 mm for 600 turns.

On the sample cell 2, a vent hole 6 having a circular cross-section with a diameter of 1.0 mm and an inlet/outlet channel 5 having a circular cross-section with a diameter of 2.5 mm are provided on the uppermost part and on the undermost part of the cylindrical cavity, respectively.

The inlet/outlet channel 5 is connected to the reservoir 1 through a tubular path 7 with a diameter of 2.5 mm. The reservoir 1 is placed on an elevator 8.

In the following paragraphs, a description will be made on a manner of operating the apparatus for transfusing liquid.

First, a specimen to be measured is supplied from a beaker or the like to the reservoir 1. In a case of employing the apparatus for supplying the specimen in an urinalysis equipment, urination may be performed directly into the reservoir 1.

Herein, at supplying the specimen to the reservoir 1, the height of the reservoir 1 is adjusted first by the elevator 8 so that the level of the specimen in the reservoir 1 is lower than that of the inlet/outlet channel 5 of the sample cell 2. In a case of bubbling in the specimen at supplying, it is preferable to allow the reservoir to stand by for a certain time until the produced bubbles have finished their upwards movement.

After the upwards movement of the bubbles being finished, the reservoir 1 is moved up by the elevator 8. At that time, the sample cell 2 remains to be fixed. When the level of the specimen in the reservoir 1 rises higher than the inlet/outlet channel 5, the specimen in the reservoir 1 is introduced into the sample cell 2. When the level of the specimen in the reservoir 1 rises higher than an optical path by further moving the reservoir 1 up, the measurement on the optical characteristics of the specimen is made possible. Herein, an opening 7a of the tubular path 7 at the side of the reservoir 1 is arranged so as to be positioned below the level of the specimen in the reservoir 1, around the time of introducing the specimen into the sample cell 2. That is, it may be arranged at the undermost end of the side wall of the reservoir 1 as shown in FIG. 1, or it may be arranged at the bottom or, as far as the condition is fulfilled, at any position of the side wall separated from the undermost part.

When the specimen is introduced into the sample cell 2, air inside the sample cell 2 is expelled through a vent hole 6. In a case of permitting the axis of the cylindrical cavity to have an inclination and where the specimen is introduced into the sample cell 2 through the undermost end in particular, the specimen is introduced into the sample cell 2 more smoothly. By doing so, the inclusion of the bubbles in the specimen in the sample cell 2 hardly occurs.

When the specimen is expelled from the sample cell 2, the reservoir 1 is moved down, and the specimen held in the sample cell 2 is returned to the reservoir 1 through the inlet/outlet channel 5. At that time, air flows into the sample cell 2 through the vent hole 6.

Washing the inside of the sample cell 2 may be done by injecting water or a cleaning solution into the reservoir 1, and transfusing it into the sample cell 2 in a manner similar to the above-mentioned and then expelling it therefrom.

In a case of replacing the specimen in the sample cell 2 with another one, and where the specimen is in a sufficient amount, the replacement may be done by injecting a fresh specimen into the reservoir 1, and transfusing the fresh specimen into the sample cell 2 in a similar manner to the above-mentioned, thereby expelling the examined specimen from the sample cell 2 through the vent hole 6. In this manner, the specimen in the sample cell can be replaced with fresh one. In a case of washing, a similar procedure may also be followed for the washing.

By virtue of the above-mentioned configuration, it is possible to introduce the specimen into the sample cell which has been previously installed in the optical system without the undesirable inclusion of the bubbles. In addition, there is no need for detaching the sample cell from the optical system, in the expelling of the specimen from the sample cell and the replacing of the specimen, as well as in the washing of the cell. Therefore, a measurement on the optical characteristics can be carried with high accuracy and the operability is greatly improved.

EXAMPLE 2

Figure 2:
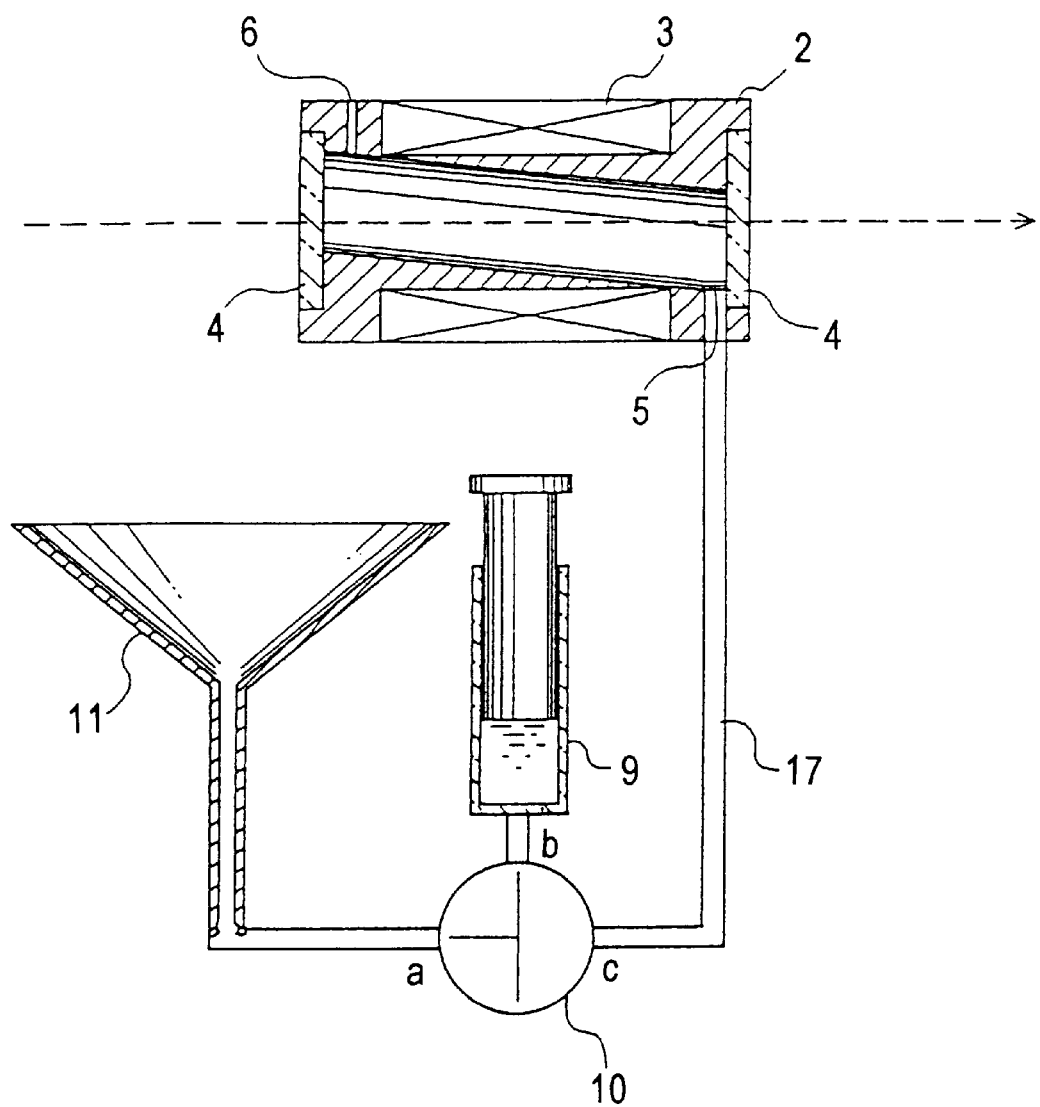
FIG. 2 is a schematic view for showing the configuration of an apparatus for transfusing liquid in another embodiment of the present invention.

An outline of the apparatus for transfusing liquid in this embodiment is shown in FIG. 2, wherein parts and components used in Example 1 having the same functions are tagged with the identical reference numerals.

The sample cell 2 used in this embodiment is similar to that used in Example 1. One end of a tubular path 17 is connected to the inlet/outlet channel 5, but another end thereof is connected to a channel "c" of a three-way cock 10. Another channel "b" of the three-way cock 10 is connected to a syringe 9, and a further end "a" is connected to a funnel 11 via a tubular path 18.

First, the specimen is charged into the funnel 11. In a case of employing this apparatus as a component of the urinalysis equipment, urination may be performed directly into this funnel 11. Then, by permitting the channel "a" of the three-way cock 10 to communicate with the channel "b", the specimen is sucked up into the syringe 9.

If bubbles are produced in the specimen sucked up in the syringe 9 at sucking up, the syringe 9 is permitted to stand by for a certain period until the bubbles move upward and stop there. After the movement of the bubbles being stopped, the specimen is introduced into the sample cell 2 by permitting the channel "b" of the three-way cock 10 to communicate with the channel "c" and driving the syringe 9. After introducing the specimen into the sample cell 2 until the level of the introduced specimen rises higher than the optical path, the measurement is conducted. By virtue of arranging the syringe 9 so that the plunger is directed upwards in particular, it is possible to introduce the specimen into the sample cell 2, while bubbles in the syringe 9 being trapped and collected therein. In this manner, it is possible to prevent the inclusion of the bubbles in the specimen in the sample cell 2.

When the specimen is expelled from the sample cell 2, the specimen is returned to the funnel 11 by permitting the channel "b" of the three-way cock 10 to communicate with the channel "c", then sucking the specimen in the sample cell 2 up into the syringe 9, and permitting the channel "a" of the three-way cock 10 to communicate with the channel "b". At washing the inside of the sample cell 2, water or a cleaning solution is transfused into the sample cell in a manner similar to the above-mentioned after charging it in the funnel 11. Then, the water or cleaning solution is expelled therefrom after washing. Alternatively, the specimen which had previously been introduced into the sample cell may be replaced with a fresh specimen or a cleaning solution by transfusing the fresh specimen or the cleaning solution into the sample cell 2 holding the previously introduced specimen.

In addition, in place of the funnel 11, the reservoir 1 of Example 1 may be used. Further, as the tubular path 18, a flexible rubber tube may be used and one open end of the flexible tube may be immersed in the specimen contained in a bowl.

Moreover, a technical advantage similar to that of the above-mentioned may be obtained without using the three-way cock 10 if the connection between the syringe 9 and the tubular path 17 is adequately cut and by directly sucking up the specimen or the cleaning solution such as water using the syringe 9 and expelling it from the sample cell 2.

As mentioned above, the syringe 9 of the apparatus for transfusing liquid of this embodiment substantially fulfill the combined function of the reservoir 1 and the elevator 8 in Example 1.

EXAMPLE 3

Figure 3:
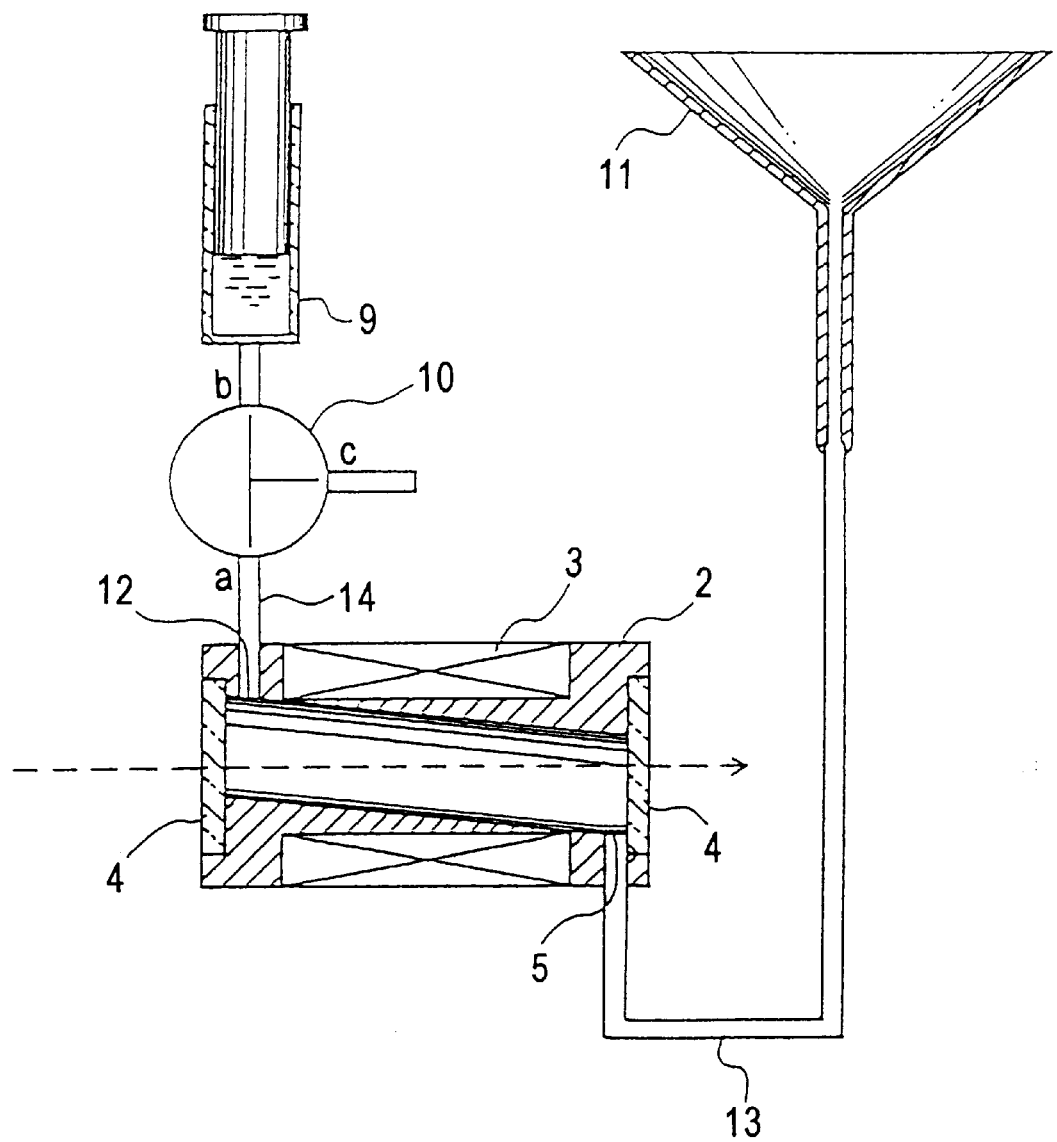
FIG. 3 is a schematic view for showing the configuration of an apparatus for transfusing liquid in a further embodiment of the present invention.

An apparatus for transfusing liquid in this embodiment is shown in FIG. 3. In the figure, the identical reference numerals are used for designating the already disclosed parts and components.

In the apparatus, a sample cell 2 similar to that used in Example 1 is used. In place of the vent hole 6, a suction hole 12 having a diameter of 2.5 mm is however provided on the sample cell 2.

In addition, the apparatus uses a syringe 9, a three-way cock 10 and a funnel 11 similar to those used in EXAMPLE 2. The suction hole 12 of the sample cell 2 is connected to a channel "a" of the three-way cock 10 via a tubular path 14. A channel "b" of the three-way cock 10 is connected to the syringe 9. An inlet/outlet channel 5 of the sample cell 2 is connected to the funnel 11 via a tubular path 13.

The specimen to be measured is supplied to the funnel 11. In a case of using this apparatus as a component of the urinalysis equipment, urination may be performed directly to this funnel 11.

Then, by permitting the channel "a" of the three-way cock 10 to communicate with the channel "b", and by sucking the specimen up using the syringe 9, the specimen in the funnel 11 is introduced into the sample cell 2. The measurement is conducted after permitting the level of the specimen in the sample cell 2 to be higher than the optical path.

By virtue of the above-mentioned configuration, even if the bubbles had been produced by the passage of the specimen through the tubular path 13 during the charging of the specimen to the funnel 11 and are eventually included in the sample cell 2, it is possible to remove the bubbles into the syringe 9 effectively by sucking them up into the syringe 9. By introducing the specimen into the sample cell again after the bubbles sucked-up by the syringe 9 have reached the upper level of the specimen, it is possible to prevent the inclusion of the bubbles in the sample cell 2.

At expelling the specimen from the sample cell 2, the specimen is once sucked up from the sample cell 2 by the syringe 9 while permitting the channel "a" of the three-way cock 10 to communicate with the channel "b", then the channel "b" is permitted to communicate with the channel "c" to expel the specimen from the syringe 9 through the channel "c". If the whole specimen can not be expelled at one operation of the syringe 9, the same operation may be repeated.

At washing the inside of the sample cell 2, water or a cleaning solution is supplied to the sample cell 2 in a manner similar to the case of the specimen after charging it into the funnel 11. Then, it is expelled therefrom after washing. The washing may alternatively be performed by permitting the three-way cock 10 to communicate the channel "b" with the channel "c" to introduce water or the cleaning solution into the syringe 9 through the channel "c", and thereafter introducing it from the syringe 9 into the sample cell 2 by permitting the three-way cock 10 to communicate the channel "a" with the channel "b".

The employment of the three-way cock 10 is not imperative, and the function of expelling the specimen from the sample cell 2 to the side of the funnel 11 may, for instance, also be performed by driving the syringe 9.

EXAMPLE 4

In this embodiment, a description will be made on the case of employing the apparatus for transfusing liquid of Example 3 for the specimen supply of a polarimeter.

Figure 4:
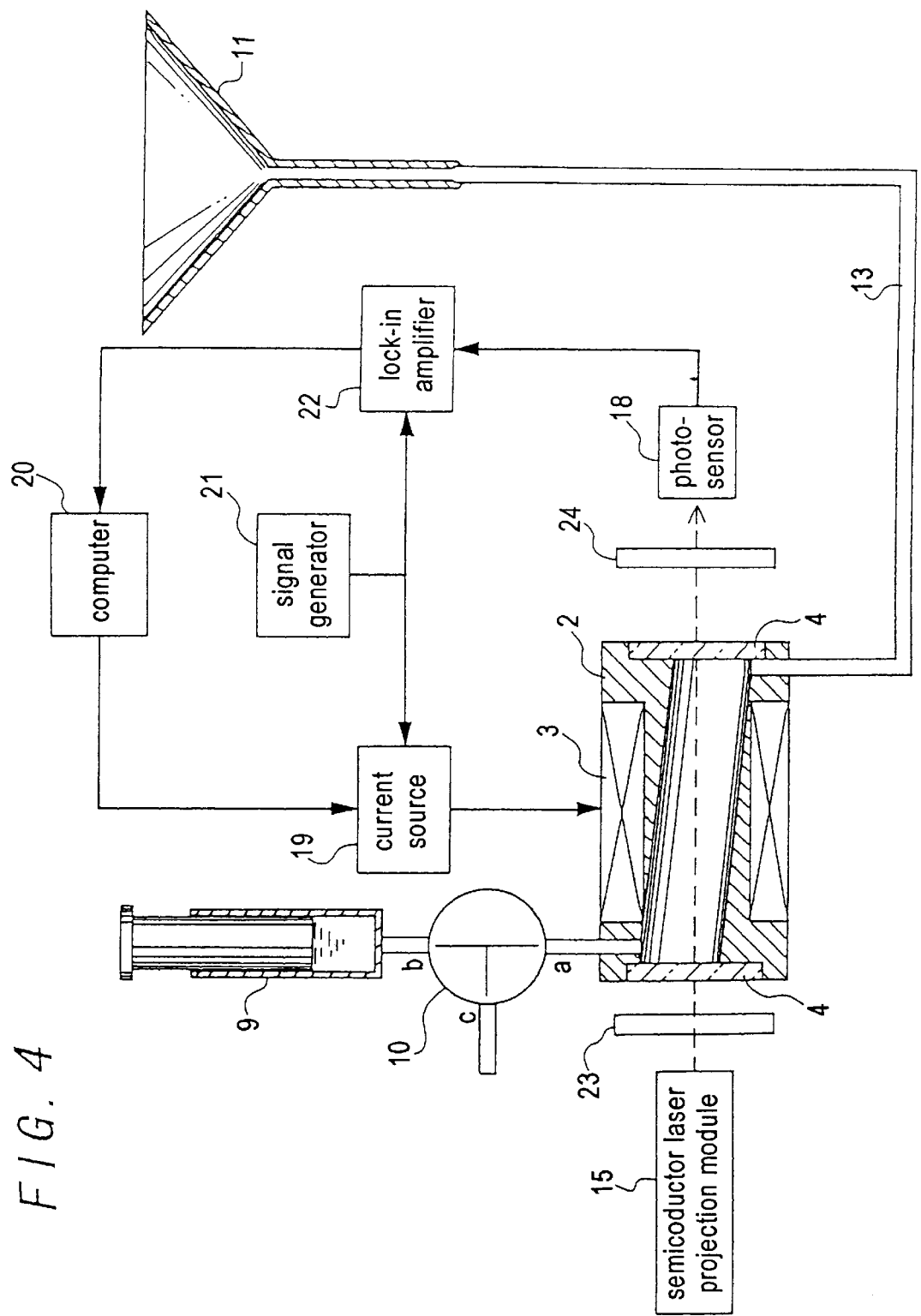
FIG. 4 is a schematic view for showing the configuration of a polarimeter in a still further embodiment of the present invention.

A configuration of the polarimeter of this example is shown in FIG. 4, wherein the identical reference numerals are used for designating the already disclosed parts and components.

A semiconductor laser projection module 15 emits a substantial parallel laser beam (hereinafter, simply referred to as "light") having a wavelength of 780 nm and an elliptical cross-section with a longer axis of about 4 mm and a shorter axis of about 2 mm. The semiconductor laser projection module 15 permits the semiconductor laser for the projection to continuously oscillate by a semiconductor laser driving circuit installed therein.

A polarizer 23 transmits only a polarized component in a specified direction of the light projected by the semiconductor laser projection module 15, for instance, only such a polarized component of the light that is parallel to the sheet of this paper.

A sample cell 2 receives the light projected by the semiconductor laser projection module 15 and transmitted through the polarizer 23. The sample cell permits the received light to transmit through the inside thereof.

An analyzer 24 transmits only a polarized component in a specified direction of the light transmitted through the sample cell 2. Herein, the analyzer 24 and the polarizer 23 are arranged in an orthogonal Nicol's state. That is, in a case wherein the polarizer 23 transmits only a polarized component of the light that is parallel to the sheet of this paper, the analyzer 24 is so arranged as to transmit only a polarized component of the light perpendicular to the sheet of this paper. A photosensor 25 detects the light transmitted through the analyzer 24.

A computer 20 issues a command signal to a current source 19 for sweeping a current to be flown through the coil 3 in a range from −5 A to 5 A. A signal generator 21 supplies a vibration-modulating signal at 1.3 kHz to a current source 19. The current source 19 converts the vibration-modulating signal from the signal generator 21 into a vibration-modulating current signal having an amplitude of 0.02 A and supplies the current signal to the coil 3 after superimposing the swept current signal commanded by the computer 20 thereon.

A lock-in amplifier 22 performs a phase sensitive detection on the output signal from the photosensor 25 with reference to the vibration-modulated signal from the signal generator 21. Since the output signal of this lock-in amplifier 22 corresponds to an angular frequency component in the output signal of the photosensor 25, a time point during the sweeping process when the output signal of this lock-in amplifier 22 reaches zero is found to be an extinction point.

The computer 20 also records and analyzes the output signal of this lock-in amplifier 22.

A measurement is actually conducted at 20° C. by the use of the above-mentioned polarimeter on optical activities of pure water and a sucrose aqueous solution with a concentration of 250 mg/dl.

Figure 5:
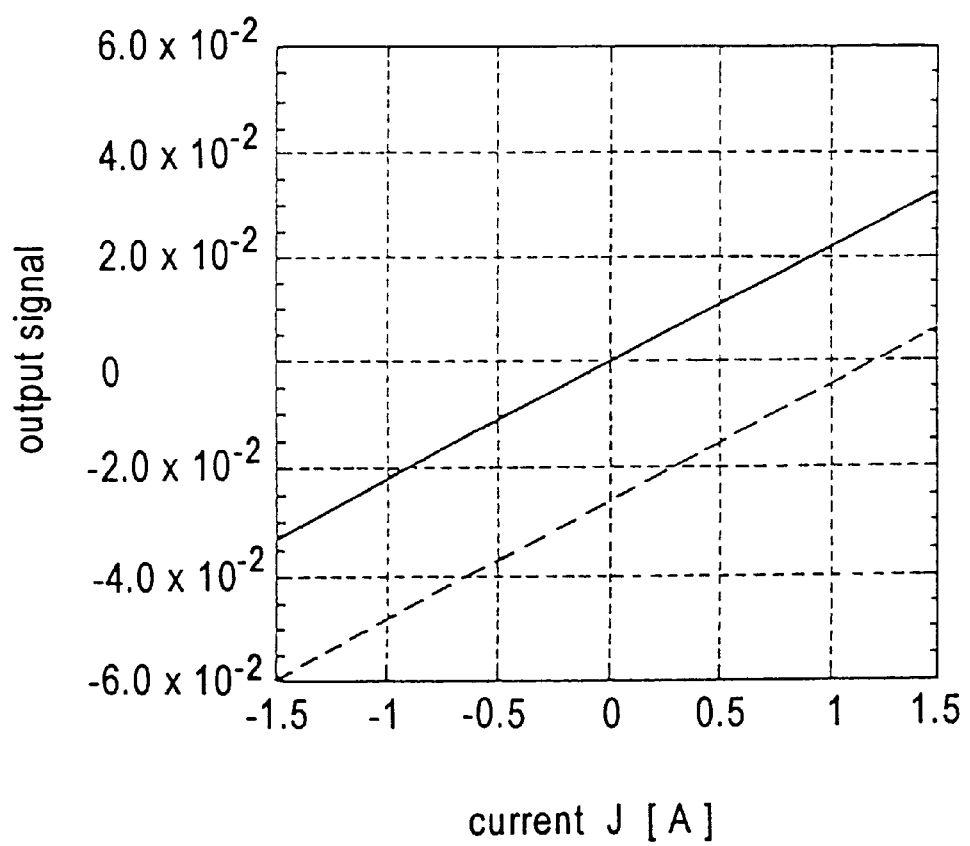
FIG. 5 is a characteristic diagram showing the relationship between the current "J" supplied to the coil and the output signal of the lock-in amplifier, obtained by using the same polarimeter, of pure water and a sucrose aqueous solution.

The output signal of this lock-in amplifier 22 obtained by sweeping the current to be flown through the coil 3 in a range from −1.5 A to 1.5 A is shown in FIG. 5. In FIG. 5, the abscissa represents the current "J" to be flown through the coil 3 and the ordinate represents the output signal of this lock-in amplifier 22 (arbitrary value).

In this diagram, the solid line indicates a result of the measurement on the pure water which does not demonstrate an optical activity. A time point when "J" equals zero is the extinction point. This is a state where no magnetic field is applied to the pure water as the specimen and no rotation of angle in the direction of the polarization due to optical Faraday effect occurs.

In contrast, the dashed line in the diagram indicates a result of the measurement on the sucrose aqueous solution. In this case, a time point when "J" is 1.21 A corresponds to the extinction point. That is, the dashed line is a straight line obtained by parallel shifting of the solid line as much as a width of +1.21 A. The displacement in the extinction points corresponds to the angle of rotation due to the specimen.

Further, measurements are additionally conducted at 20° C. by using the above-mentioned polarimeter on optical activities of sucrose aqueous solutions with concentrations of 50, 100, 150 and 250 mg/dl in turn.

First, the sucrose aqueous solution with a concentration of 50 mg/dl is charged into the funnel 11 and the sucked up into the syringe 9, thereby to introduce the specimen into the sample cell 2, and the optical activity thereof is measured. After the measurement being finished, the sucrose aqueous solution in the sample cell 2 is sucked up into the syringe 9 and expelled therefrom through the channel "c" of the three-way cock 10. Next, water is charged into the funnel 11 and transfused into the sample cell 2, thereby to wash the inside of the sample cell 2. After the water is expelled, the sucrose aqueous solution with concentration of 100 mg/dl is charged into the funnel 11 and introduced into the sample cell 2 in a similar manner. Then, the optical activity of the solution is measured. A similar procedure is repeated in the measurement on the other aqueous solutions.

Figure 6:
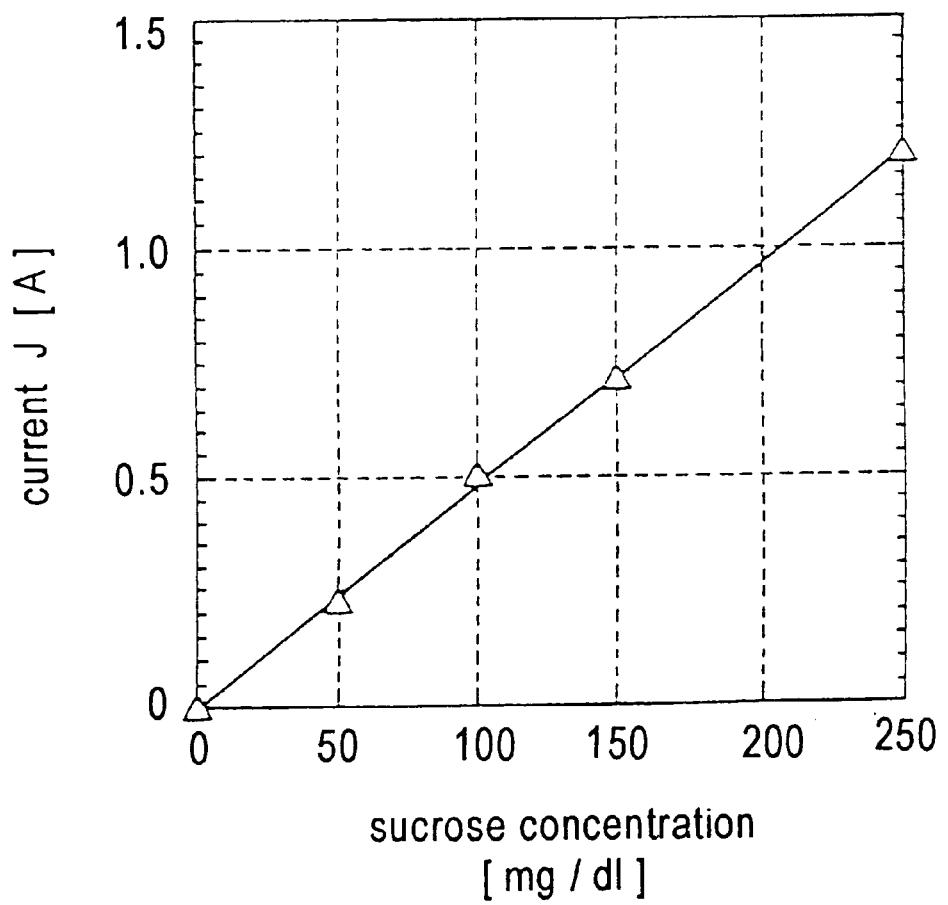
FIG. 6 is a characteristic diagram showing the relationship between the concentration of sucrose aqueous solution and the current "J" when an extinction point is reached, in the same polarimeter.

The results of the measurements are shown in FIG. 6. In this diagram, the abscissa represents the sucrose concentration and the ordinate represents the current "J" at which an extinction point appears. As clearly shown by the diagram, it is confirmed that the relationship between the concentration and the measurement value is approximated by a linear equation. The result indicates that the inclusion of bubbles in the sample cell can be prevented and this resulting a measurement with high accuracy, according to the polarimeter of this embodiment. In addition, by performing the washing of the inside of the cell, it is possible to effectively conduct the measurements on a large number of specimens.

As previously-described, the polarimeter of this embodiment can measure the sucrose concentration of the solution with high accuracy. It is also possible to perform a measurement with high accuracy on albumin or glucose which demonstrates an optical activity as sucrose. That is, by applying this polarimeter to the urinalysis, an accurate test on the urine sugar value or the urine albumin concentration can be conducted. In addition, since the replacement of the specimen or the washing of the cell is easy, a burden on the user for this operation can greatly be reduced.

Further, as a means for moving the specimen, a pump may well be used in place of the elevator or the syringe used in the foregoing embodiments.

According to the present invention, it is possible to provide the apparatus for transfusing liquid in the optical characteristic measurement with a high operability and at a low cost. In addition, since this apparatus can prevent the inclusion of the bubbles produced during the introduction of the specimen into the sample cell, it is also possible to provide a small-sized polarimeter and an urinalysis equipment having an excellent operability at a low cost.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

We claim:

1. A method for transfusing a liquid specimen for an optical characteristic measurement including the steps of:
preparing an optical characteristic measurement apparatus comprising,
a reservoir for temporarily accommodating a liquid specimen to be measured,
a sample cell for holding said specimen and for permitting a projected light to transmit through the held specimen, and
a tubular path for connecting between said sample cell at the portion being in contact with the held specimen and said reservoir;
supplying the specimen accommodated in the reservoir into said reservoir;
allowing the reservoir to stand for a certain time; and
introducing the specimen accommodated in said reservoir into said sample cell through said tubular path.

2. The method for transfusing a liquid specimen for an optical characteristic measurement in accordance with claim 1, further comprising the steps of:
transfusing the specimen introduced in said sample cell, into said reservoir through said tubular path, and removing the specimen transfused into said reservoir therefrom.

3. The method for transfusing a liquid specimen for an optical characteristic measurement in accordance with claim 1, further comprising the steps of:

supplying a cleaning solution into said reservoir, after removing said specimen from said reservoir;

introducing the cleaning solution accommodated in the reservoir into said sample cell through said tubular path;

transfusing the cleaning solution introduced in said sample cell into said reservoir through said tubular path; and removing the cleaning solution transfused into said reservoir therefrom.

4. The method for transfusing a liquid specimen for an optical characteristic measurement in accordance with claim 1, wherein another liquid specimen to be measured or a cleaning solution is further supplied to said sample cell, in a state where the previously introduced specimen remains in said sample cell, thereby to expel the specimen remaining in said sample cell and replace the remaining specimen by said another liquid specimen or said cleaning solution.

5. The method for transfusing a liquid specimen for an optical characteristic measurement in accordance with claim 1, wherein said specimen or a cleaning solution is transfused between said reservoir and said sample cell by moving said reservoir or said sample cell upwards and downwards.

6. The method for transfusing a liquid specimen for an optical characteristic measurement in accordance with claim 1, wherein said specimen is transfused between said reservoir and said sample cell, by sucking said specimen in said reservoir or in said sample cell up using a syringe arranged on a route of said tubular path then releasing the sucked-up specimen to the other side.

7. The method for transfusing a liquid specimen for an optical characteristic measurement in accordance with claim 6, wherein said syringe is so arranged that a plunger thereof is directed upward.

8. A method for transfusing a liquid specimen for an optical characteristic measurement including the steps of:

preparing an optical characteristic measurement apparatus comprising,
  a reservoir for temporarily accommodating a liquid specimen to be measured,
  a sample cell for holding said specimen and for permitting a projected light to transmit through the held specimen, and
  a tubular path for connecting between said sample cell at the portion being immersed in the holding specimen and said reservoir;

injecting the specimen or a cleaning solution into said reservoir; and introducing said specimen or said cleaning solution accommodated in said reservoir into said sample cell through said tubular path by sucking up through an opening arranged at the top end of said sample cell.

9. The method for transfusing a liquid specimen for an optical characteristic measurement in accordance with claim 8, wherein the specimen introduced in said sample cell is expelled by sucking it up from said opening.

10. The method for transfusing a liquid specimen for an optical characteristic measurement in accordance with claim 8, wherein another liquid specimen to be measured or a cleaning solution is further supplied to said sample cell, in a state where the previously introduced specimen remains in said sample cell, thereby to expel the specimen remaining in said sample cell and replace the remaining specimen with said another liquid specimen or said cleaning solution.

11. An apparatus for transfusing a liquid specimen for an optical characteristic measurement comprising;

a reservoir for temporarily accommodating a liquid specimen to be measured;

a sample cell for holding said specimen and for permitting a projected light to transmit through the held specimen;

a tubular path for connecting the bottom of said sample cell with said reservoir at a portion to be immersed in said accommodated specimen; and an elevator for moving at least one of said reservoir and said sample cell upward and downwards.

12. An apparatus for transfusing a liquid specimen for an optical characteristic measurement comprising; a three-way cock whose one channel is connected to a sample cell for holding a liquid specimen to be measured, and a syringe and a reservoir for accommodating the specimen, each connected to one of the other two channels of said three-way cock, respectively.

13. The apparatus for transfusing a liquid specimen for an optical characteristic measurement in accordance with claim 12, wherein said syringe is so arranged that a plunger thereof is placed upper side.

14. An apparatus for transfusing a liquid specimen for an optical characteristic measurement comprising a syringe for expelling a liquid specimen held in a sample cell.

15. The apparatus for transfusing a liquid specimen for an optical characteristic measurement in accordance with claim 14, wherein said syringe is connected to said sample cell through a three-way cock.

16. A polarimeter utilizing the apparatus for transfusing a liquid specimen for an optical characteristic measurement in accordance with claim 11, further comprising:

a monochrome light source for projecting a substantial parallel light;

a polarizer for transmitting only a polarized component in a specified direction of said substantial parallel light;

a coil for applying a magnetic field in the direction of an optical path of said substantial parallel light transmitting through said specimen in said sample cell;

a current source for supplying a current to said coil;

a magnetic field sweeping means for sweeping the current to be flown through said coil;

a magnetic field modulating means for modulating the current to be flown through said coil;

an analyzer for transmitting only a polarized component in another specified direction of said light transmitted through said specimen;

a photosensor for detecting the light transmitted through said analyzer;

a lock-in amplifier for conducting a phase sensitive detection on an output signal of said photosensor with reference to a vibration modulation signal from said magnetic field modulating means; and a processing unit for calculating an optical activity of said specimen based on a magnetic field sweeping signal of said magnetic field sweeping means and the output signal from said lock-in amplifier.

17. The polarimeter in accordance with claim 16, wherein said specimen is urine.

18. A polarimeter utilizing the apparatus for transfusing a liquid specimen for an optical characteristic measurement in accordance with claim 12, further comprising:

a monochrome light source for projecting a substantial parallel light;

a polarizer for transmitting only a polarized component in a specified direction of said substantial parallel light;

a sample cell for holding the specimen, which allows said substantial parallel light transmitted through said polarizer to transmit therethrough;

a coil for applying a magnetic field in the direction of an optical path of said substantial parallel light transmitting through said specimen in said sample cell;

a current source for supplying a current to said coil;

a magnetic field sweeping means for sweeping the current to be flown through said coil;

a magnetic field modulating means for modulating the current to be flown through said coil;

an analyzer for transmitting only a polarized component in another specified direction of said light transmitted through said specimen;

a photosensor for detecting the light transmitted through said analyzer;

a lock-in amplifier for conducting a phase sensitive detection on an output signal of said photosensor with reference to a vibration modulation signal from said magnetic field modulating means; and processing unit for calculating an optical activity of said specimen based on a magnetic field sweeping signal of said magnetic field sweeping means and the output signal from said lock-in amplifier.

19. The polarimeter in accordance with claim 18, wherein said specimen is urine.

20. A polarimeter utilizing the apparatus for transfusing a liquid specimen for an optical characteristic measurement in accordance with claim 14, further comprising:

a monochrome light source for projecting a substantial parallel light;

a polarizer for transmitting only a polarized component in a specified direction of said substantial parallel light;

a sample cell for holding the specimen, which allows said substantial parallel light transmitted through said polarizer to transmit therethrough;

a coil for applying a magnetic field in the direction of an optical path of said substantial parallel light transmitting through said specimen in said sample cell;

a current source for supplying a current to said coil;

a magnetic field sweeping means for sweeping the current to be flown through said coil;

a magnetic field modulating means for modulating the current to be flown through said coil;

an analyzer for transmitting only a polarized component in another specified direction of said light transmitted through said specimen;

a photosensor for detecting the light transmitted through said analyzer;

a lock-in amplifier for conducting a phase sensitive detection on an output signal of said photosensor with reference to a vibration modulation signal from said magnetic field modulating means; and a processing unit for calculating an optical activity of said specimen based on a magnetic field sweeping signal of said magnetic field sweeping means and the output signal from said lock-in amplifier.

21. The polarimeter in accordance with claim 20, wherein said specimen is urine.

* * * * *